(12) United States Patent
Londesborough et al.

(10) Patent No.: US 7,527,951 B2
(45) Date of Patent: *May 5, 2009

(54) ENGINEERING FUNGI FOR THE UTILISATION OF L-ARABINOSE

(75) Inventors: John Londesborough, Helsinki (FI); Merja Penttilä, Helsinki (FI); Peter Richard, Helsinki (FI)

(73) Assignee: Valtion Teknillinen Tutkimuskeskus (FI)

(*) Notice: Subject to any disclaimer, the term of this patent is extended or adjusted under 35 U.S.C. 154(b) by 933 days.

This patent is subject to a terminal disclaimer.

(21) Appl. No.: 10/257,821

(22) PCT Filed: Feb. 15, 2002

(86) PCT No.: PCT/FI02/00125

§ 371 (c)(1),
(2), (4) Date: Mar. 10, 2003

(87) PCT Pub. No.: WO02/066616

PCT Pub. Date: Aug. 29, 2002

(65) Prior Publication Data

US 2003/0186402 A1 Oct. 2, 2003

(30) Foreign Application Priority Data

Feb. 16, 2001 (FI) .................................. 20010308

(51) Int. Cl.
*C12P 7/06* (2006.01)
*C12N 1/18* (2006.01)
*C12N 1/16* (2006.01)
*C12N 15/74* (2006.01)

(52) U.S. Cl. ...................... 435/171; 435/69.1; 435/161; 435/252.3; 435/254.1

(58) Field of Classification Search ........................ None
See application file for complete search history.

(56) References Cited

U.S. PATENT DOCUMENTS 7,091,014 B1 * 8/2006 Aristidou et al. ............ 435/161

FOREIGN PATENT DOCUMENTS

EP 450430 A2 * 10/1991
WO 9850524 11/1998
WO WO 9946363 A1 * 9/1999

OTHER PUBLICATIONS

Richard et al. (Journal of Biological Chemistry, 1991, vol. 276, No. 44, pp. 40631-40637).*
Aarnikunnas et al. (Applied and Environmental Microbiology, Jan. 2006, vol. 72 No. 1, pp. 368-377).*
"Characterization and Complementation of a Pichia Stipitis Mutant Unable to Grow on D-xylose or L-arabinose," by N.Q. Shi et al., National Library of Medicine, Medline Accession No. 10849789, *Applied Biochemistry and Biotechnology*, Spring 2000, 84-86:201-16. Abstract only.
"Expression of E. coli araBAD Operon Encoding Enzymes for Metabolizing L-arabinose in Saccharomyces cerevisiae," by M. Sedlak and N. Ho, *Enzyme and Microbial Technology*, vol. 28, 2001, pp. 16-24.
"Extracellular Arabinases in Aspergillus nidulans: The Effect of Different cre Mutations on Enzyme Levels," by P. van der Veen et al., *Archives of Microbiology*, vol. 162, 1994, pp. 433-440.
"Isolation and Characterization of Two Xylitol Dehydrogenases From Aspergillus niger," by C.F.B. Witteveen et al., *Microbiology*, vol. 140, 1994, pp. 1679-1685.
"L-arabinose and D-xylose Catabolism in Aspergillus niger," by C.F.B. Witteveen et al., *Journal of General Microbiology*, vol. 135, 1989, pp. 2163-2171.
"Molecular Cloning, Expression and Tissue Distribution of Hamster Diacetyl Reductase. Identity With L-xylulose Reductase," by S. Ishikura et al., *Chemico-Biological Interactions*, vol. 130-32, Jan. 30, 2001, pp. 879-889.
"Screening for L-arabinose Fermenting Yeasts," by B.S. Dien et al., *Applied Biochemistry & Biotechnology*, vol. 57/58, 1996, pp. 233-240.
Amore, R. et al. (1991) "Cloning and Expression in *Saccharomyces cerevisiae* of the NAD(P)H-dependent Xylose Reductase-Encoding Gene (XYL1) from the Xylose Assimilating Yeast *Pichia stipitis*," Gene 109, 89-97.
Billard, P. et al. (1995) "Isolation and Characterisation of the Gene Encoding Xylose Reductase From *Kluyveromyces lactis*," Gene 162, 93-97.
Blomqvist, K. et al. (1991) "Chromosomal Integration and Expression of Two Bacterial Alpha-acetolactate Decarboxylase Genes in Brewer's Yeast," Appl. Environ. Microbiology 57, 2796-2803.
Bolen, P.L. et al. (1996) "Sequence and Analysis of an Aldose Reductase Gene From Xylose Fermenting Yeast *Pachysolen tannophilus*," Yeast 12, 1367-1375.
Chan, E. et al. (1989) "Metabolism of D-xylose in *Schizosaccharomyces pombe* Cloned With a Xylose Isomerase Gene," Appl. Microbiology & Biotechnology 31, 524-528.
Chiang, C. et al. (1960) "A new pathway of pentose metabolism," Biochem. Biophys. Res. Commun. 3, 554-559.
Chiang, C. et al. (1959) "D-xylose metabolism by cell free extracts of *Penicillium chrysogenum*," Biochem. Biophys. Acta. 35, 454-463.
Doten, R.C. et al. (1985) "Characterisation of Xylitol-utilizing mutants of *Erwinia uredovora*," Journal of Bacteriology 161, 529-533.
Gietz, D. et al. (1992) "Improved method for high efficiency transformation of intact yeast cells," Nucleic Acids Res. vol. 20, No. 6, 1425.

(Continued)

*Primary Examiner*—Robert A Zeman
(74) *Attorney, Agent, or Firm*—Rothwell, Figg, Ernst & Manbeck, p.c.

(57) ABSTRACT

A fungal microorganism can be engineered by means of genetic engineering to utilise L-arabinose. The genes of the L-arabinose pathway, which were unknown, i.e. L-arabinitol 4-dehydrogenase and L-xylulose reductase, were identified. These genes, together with the known genes of the L-arabinose pathway, form a functional pathway. This pathway can be introduced to a fungus, which is completely or partially lacking this pathway.

1 Claim, 5 Drawing Sheets

OTHER PUBLICATIONS

Hacker, B. et al. (1999) "Xylose utilisation: cloning and characterisation of the xylose reductase from *Candida tenius*," Biol. Chem. 380, 1395-1403.

Henderson, R.C. et al. (1985) "The transformation of brewing yeasts with a plasmid containing the gene for copper resistance," Curr. Genetics 9, 133-38.

Hickman, J. et al. (1959) "A sensitive and stereospecific enzymatic assay for xylulose," Journal Biol. Chem. 234, 758-761.

Ho, N. et al. (1989) "Cloning of yeast Xylulokinase gene by complementation of *E. coli* and yeast mutations," Enzyme Microb. Technol. 11, 417-421.

Kotter, P. et al. (1990) "Isolation and characterisation of the *Pichia stipitis* xylitol dehydrogenase gene, XYL2, and construction of a xylulose-utilizing *Saccharomyces cerevisiae* transformant," Curr. Genetics 18, 493-500.

Kristo, P. et al. (1996) "Protein purification and cloning and characterization of the cDNA and gene for xylose isomerase of barley," Eur. J. Biochem. 237, 240-246.

Kuhn, A. et al. (1995) "Purification and partial characterisation of an aldo-keto reductase from *Saccharomyces cerevisiae*," Applied and Environmental Microbiology, vol. 61, No. 4, 1580-1585.

McMillan, J.D. et al. (1994) "Arabinose utilisation by xylose fermenting yeasts and fungi," Appl. Biochem. Biotechnol. vol. 45/46, 569-584.

Mandels, M. et al. (1969) "The production of cellulases," Adv. Chem. Ser. 95, 391-414.

Mellor, J. et al. (1983) "Efficient Synthesis of Enzymatically Active Calf Chymosin in *Saccharomyces cerevisiae*," Gene 24, 1-4.

Moes, C.J. et al. (1996) "Cloning and Expression of the clostridium thermo-sulfurogenes d-xylose isomerase gene (xylA) in *Saccharomyces cerevisiae*," Biotechnology Letters, vol. 18, No. 3, 269-274.

Margolles-Clark, E. et al. (1996) "Cloning and genes encoding alpha-L-arabinofuranosidase and beta-xylosidase from *Trichoderma reesei* by expression in *Saccharomyces cerevisiae*," Applied and Environmental Microbiology, vol. 62, No. 10, 3840-46.

Richard, P. et al. (1999) "Evidence that gene YLR070c of *Saccharomyces cerevisiae* encodes a xylitol dehydrogenase," FEBS Letters 457, 135-138.

Richard, P. et al. (2000) "The role of xyluokinase in *Saccharomyces cerevisiae* xylulose catabolism," FEMS Microbiol. Letters 190, 39-43.

Sarthy, A. et al. (1987) "Expression of the *Escherichia coli* xylose isomerase gene in *Saccharomyces cerevisiae*," Appl. Environ. Microbiol. vol. 53, No. 9, 1996-2000.

Schrunder, J. et al. (1996) "Extranuclear expression of the bacterial xylose isomerase (xylA) and the UDP-glucose dehydrogenase (hasB) genes in yeast with *Kluyveromyces lactis* linear killer plasmids as vectors," Current Microbiology, vol. 33, 323-330.

Shaw, D.R. (1956) "Polyol dehydrogenases. 3. Galactitol dehydrogenase and D-iditol dehydrogenase," Biochem. J. 64, 394-405.

Sherman, F. et al. (1983) "Methods in Yeast Genetics—A Laboratory Manual," Cold Spring Harbor Laboratory Press, Cold Spring Harbor, NY.

Stryer, L. (1988) "Biochemistry," Freeman/New York.

Toivari, M. H. et al. (2001) "Conversion of Xylose to Ethanol by Recombinant *Saccharomyces cerevisiae*: Importance of Xylulokinase (XKS1) and Oxygen Availability," Metabolic Engineering 3, 236-249.

Verduyn, C. et al. (1985) "Properties of the NAD(P)H-Dependent Xylose Reductase From the Xylose-Fermenting Yeast *Pichia stipitis*," Biochem. J. 226, 669-677.

Tianhong, W. et al. (1999) "Isolation and Identification of Xylitol Dehydrogenase Gene From *Trichoderma reesei*," Chinese Journal of Biotechnology, vol. 14, No. 3, 179-185.

Nair et al., "Biochemical Characterization of an L-Xylulose Reductase from *Neurospora crassa*" Appl. Enviro. Microbiol. (2007) 73:2001-2004.

Sullivan et al., "Cloning Characterization, and Mutational Analysis of a Highly Active and Stable L-arabinitol 4-dehydrogenase from *Neurospora crassa*" Appl. Microbiol. Biotechnol. (2007) 77:845-852.

Suzuki et al., "Cloning and Expression of $NAD^+$-Dependent L-Arabinitol 4-Dehydrogenase Gene (ladA) of *Aspergillus oryzae*" J. of Bios. and Bioengin. (2005) 100(4):472-474.

\* cited by examiner

Fungal Pathway:
Bacterial pathway:
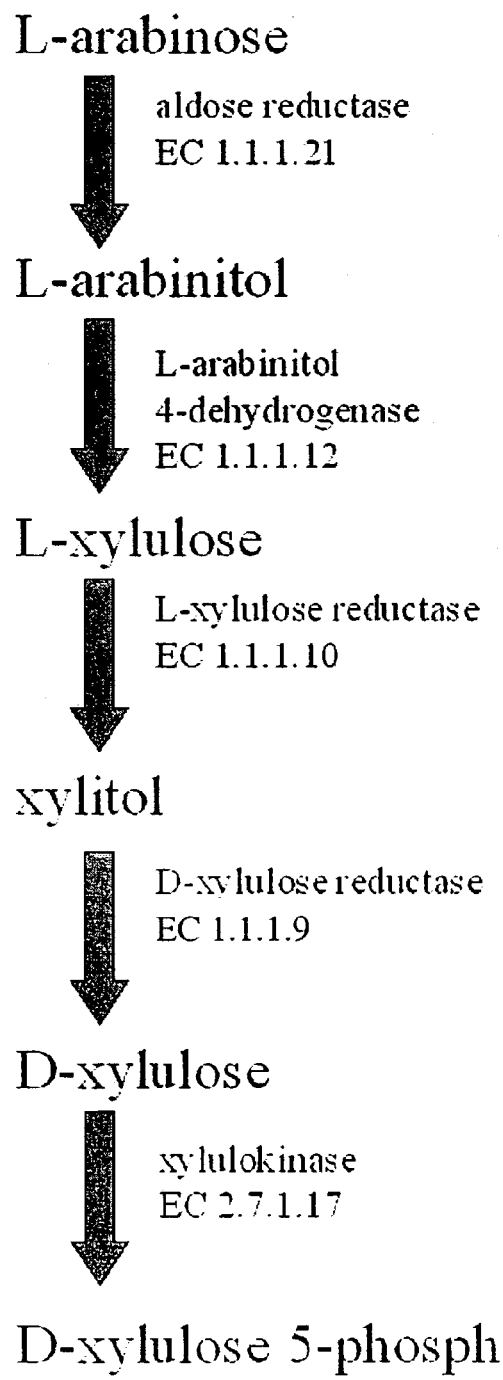
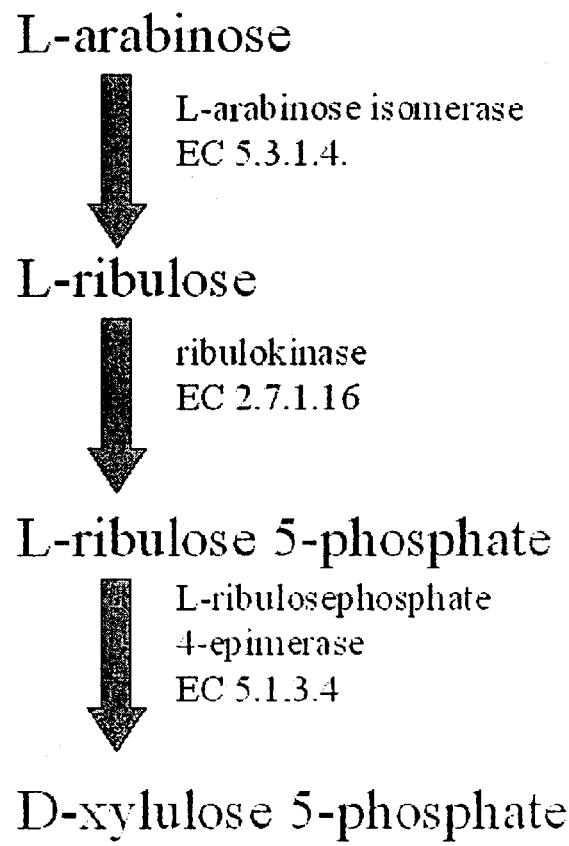
Figure 1

```
1021        AATCAGCATTCCCTTTATGAGGGCCAGTGTACGCGAGGTCGATATCCAGCTGCAGTATCG
303           I  S  I  P  F  M  R  A  S  V  R  E  V  D  I  Q  L  Q  Y  R

1081        CTACAGCAACACCTGGCCTCGTGCCATCCGGCTCATCGAGAGCGGTGTCATCGATCTATC
323           Y  S  N  T  W  P  R  A  I  R  L  I  E  S  G  V  I  D  L  S

1141        CAAATTTGTGACGCATCGCTTCCCGCTGGAGGATGCCGTCAAGGCATTTGAGACGTCAGC
343           K  F  V  T  H  R  F  P  L  E  D  A  V  K  A  F  E  T  S  A

1201        AGATCCCAAGAGCGGCGCCATTAAGGTCATGATTCAGAGCCTGGATTGAGAGTGAGGTGC
363           D  P  K  S  G  A  I  K  V  M  I  Q  S  L  D  *

1261        TACCAGGTAGAGGTAGATAATAGATAGATGATGAAGATGGAAAGACTGCGGGCGCAAGAA

1321        TCGGGCGGATAGGGAGTTGGCTGTAATGGTTTGCAAAGCAT
```

Figure 2

```
1    CTCAAACGCCTTGTTCGCCGGAGACCGCGCGCATTCACAGCTCGCCATGTCGCCTTCCGC
1                                                   M  S  P  S  A

61   AGTCGATGACGCTCCCAAGGCCACAGGGGCAGCCATCTCAGTCAAGCCCAACATTGGCGT
6     V  D  D  A  P  K  A  T  G  A  A  I  S  V  K  P  N  I  G  V

121  CTTCACAAATCCAAAACATGACCTCTGGATTAGCGAAGCTGAACCCAGCGCCGATGCCGT
26    F  T  N  P  K  H  D  L  W  I  S  E  A  E  P  S  A  D  A  V

181  CAAATCTGGCGCTGATCTGAAGCCCGGCGAGGTGACCATTGCTGTCCGCAGCACTGGTAT
46    K  S  G  A  D  L  K  P  G  E  V  T  I  A  V  R  S  T  G  I

241  CTGTGGGTATGTATAACGCTTCTGTCCACAGAGCGCAAGCGCAGAGGAGCAGCATGCTGA
66    C  G

301  ACGAAATACGAATAGTTCAGATGTCCATTTCTGGCACGCCGGCTGCATTGGGCCCATGAT
68                  S  D  V  H  F  W  H  A  G  C  I  G  P  M  I

361  CGTCGAGGGCGACCACATCCTCGGCCACGAGTCTGCCGGCGAGGTCATCGCCGTCCACCC
83    V  E  G  D  H  I  L  G  H  E  S  A  G  E  V  I  A  V  H  P

421  GACTGTCAGTAGCCTCCAAATCGGCGATCGGGTTGCCATCGAGCCCAACATCATCTGCAA
103   T  V  S  S  L  Q  I  G  D  R  V  A  I  E  P  N  I  I  C  N

481  CGCGTGCGAGCCCTGCCTGACAGGTCGATACAACGGCTGCGAAAAGGTCGAGTTCCTATC
123   A  C  E  P  C  L  T  G  R  Y  N  G  C  E  K  V  E  F  L  S

541  CACGCCGCCAGTGCCCGGACCGCTGCGACGCTACGTCAACCACCCAGCCGTTTGGTGCCA
143   T  P  P  V  P  G  P  L  R  R  Y  V  N  H  P  A  V  W  C  H

601  CAAGATTGGCAACATGTCGTGGGAGAACGGCGCGCTGCTGGAGCCCCTGAGCGTGGCTCT
163   K  I  G  N  M  S  W  E  N  G  A  L  L  E  P  L  S  V  A  L

661  GGCCGGCATGCAGAGGGCCAAGGTTCAGCTCGGTGACCCCGTGCTGGTCTGCGGCGCTGG
183   A  G  M  Q  R  A  K  V  Q  L  G  D  P  V  L  V  C  G  A  G

721  TCCGATTGGATTGGTGTCAATGCTGTGCGCTGCTGCCGCCGGTGCTTGCCCGCTTGTCAT
203   P  I  G  L  V  S  M  L  C  A  A  A  A  G  A  C  P  L  V  I

781  CACAGACATTTCAGAGAGCCGTCTGGCGTTTGCAAAGGAGATCTGCCCCCGCGTCACCAC
223   T  D  I  S  E  S  R  L  A  F  A  K  E  I  C  P  R  V  T  T

841  GCACCGCATCGAGATTGGCAAGTCGGCTGAGGAAACGGCCAAAAGCATCGTCAGCTCTTT
243   H  R  I  E  I  G  K  S  A  E  E  T  A  K  S  I  V  S  S  F

901  TGGGGGCGTCGAGCCAGCCGTGACCCTGGAGTGCACCGGTGTGGAGAGCAGCATTGCAGC
263   G  G  V  E  P  A  V  T  L  E  C  T  G  V  E  S  S  I  A  A

961  GGCCATCTGGGCCAGCAAGTTTGGAGGAAAGGTCTTTGTGATCGGCGTCGGCAAGAATGA
283   A  I  W  A  S  K  F  G  G  K  V  F  V  I  G  V  G  K  N  E
```

Figure 2, cont.

```
  1    CCCCATCCTTTGCATCGCCCATCATGCCTCAGCCTGTCCCCACCGCCAACAGACTCCTTG
  1                                M  P  Q  P  V  P  T  A  N  R  L  L

61    ATCTCTTCAGCTTGAAGGGCAAGGTCGTCGTCGTCACCGGCGCTTCCGGCCCTCGAGGCA
 13    D  L  F  S  L  K  G  K  V  V  V  V  T  G  A  S  G  P  R  G

121    TGGGAATCGAAGCTGCCCGTGGCTGCGCCGAGATGGGCGCTGACCTCGCCATCACCTACT
 33    M  G  I  E  A  A  R  G  C  A  E  M  G  A  D  L  A  I  T  Y

181    CGTCTCGCAAGGAGGGCGCGGAGAAGAACGCCGAGGAATTGACCAAGGAATACGGCGTCA
 53    S  S  R  K  E  G  A  E  K  N  A  E  E  L  T  K  E  Y  G  V

241    AAGTCAAGGTGTACAAGGTCAACCAGAGCGACTACAACGATGTTGAGCGCTTTGTGAACC
 73    K  V  K  V  Y  K  V  N  Q  S  D  Y  N  D  V  E  R  F  V  N

301    AGGTCGTGTCTGACTTTGGCAAGATCGATGCCTTTATTGCCAACGCCGGAGCCACAGCTA
 93    Q  V  V  S  D  F  G  K  I  D  A  F  I  A  N  A  G  A  T  A

361    ATAGCGGAGTTGTTGACGGCAGCGCCAGCGATTGGGACCATGTCATCCAGGTCGACCTGA
113    N  S  G  V  V  D  G  S  A  S  D  W  D  H  V  I  Q  V  D  L

421    GCGGCACCGCATACTGCGCAAAGGCTGTTGGCGCGCACTTCAAGAAGCAGGGCCACGGCT
133    S  G  T  A  Y  C  A  K  A  V  G  A  H  F  K  K  Q  G  H  G

481    CCCTTGTCATCACAGCTTCAATGTCCGGCCACGTCGCAAACTATCCCCAGGAACAGACCT
153    S  L  V  I  T  A  S  M  S  G  H  V  A  N  Y  P  Q  E  Q  T

541    CATACAACGTCGCCAAGGCCGGTTGCATCCATCTGGCGCGGTCTCTGGCCAACGAGTGGC
173    S  Y  N  V  A  K  A  G  C  I  H  L  A  R  S  L  A  N  E  W

601    GTGATTTTGCCCGCGTCAACAGCATTTCGCCCGGTTATATCGATACCGGCCTGTCCGACT
193    R  D  F  A  R  V  N  S  I  S  P  G  Y  I  D  T  G  L  S  D

661    TCATCGACGAGAAGACGCAAGAGCTGTGGAGGAGCATGATCCCCATGGGACGAAACGGCG
213    F  I  D  E  K  T  Q  E  L  W  R  S  M  I  P  M  G  R  N  G

721    ATGCCAAGGAGCTCAAGGGCGCGTATGTATATCTGGTCAGCGACGCTAGCTCGTACACGA
233    D  A  K  E  L  K  G  A  Y  V  Y  L  V  S  D  A  S  S  Y  T

781    CGGGAGCCGATATTGTGATTGACGGAGGTTACACTACACGATAAAGAAATAATGTATTGT
253    T  G  A  D  I  V  I  D  G  G  Y  T  T  R  *

841    TAGACTATAATCAATGTGACGAACAAGATTTGTGATTAAGAAAAAAAAAAAAAAAAAAAA

901    AAAACTCGAGTAATTCCGATAGA
```

Figure 3

SEQUENCE LISTING

<160> NUMBER OF SEQ ID NOS: 2

<210> SEQ ID NO 1
<211> LENGTH: 1361
<212> TYPE: DNA
<213> ORGANISM: L-arabinitol 4-dehydrogenase

<400> SEQUENCE: 1

```
ctcaaacgcc ttgttcgccg gagaccgcgc gcattcacag ctcgccatgt cgccttccgc        60
agtcgatgac gctcccaagg ccacaggggc agccatctca gtcaagccca acattggcgt       120
cttcacaaat ccaaaacatg acctctggat tagcgaagct gaacccagcg ccgatgccgt       180
caaatctggc gctgatctga agcccggcga ggtgaccatt gctgtccgca gcactggtat       240
ctgtgggtat gtataacgct tctgtccaca gagcgcaagc gcagaggagc agcatgctga       300
acgaaatacg aatagttcag atgtccattt ctggcacgcc ggctgcattg gcccatgat       360
cgtcgagggc gaccacatcc tcggccacga gtctgccggc gaggtcatcg ccgtccaccc       420
gactgtcagt agcctccaaa tcggcgatcg ggttgccatc gagcccaaca tcatctgcaa       480
cgcgtgcgag ccctgcctga caggtcgata aacggctgc gaaaaggtcg agttcctatc       540
cacgccgcca gtgcccggac cgctgcgacg ctacgtcaac cacccagccg tttggtgcca       600
caagattggc aacatgtcgt gggagaacgg cgcgctgctg gagcccctga gcgtggctct       660
ggccggcatg cagagggcca aggttcagct cggtgacccc gtgctggtct gcggcgctgg       720
tccgattgga ttggtgtcaa tgctgtgcgc tgctgccgcc ggtgcttgcc cgcttgtcat       780
cacagacatt tcagagagcc gtctggcgtt tgcaaaggag atctgccccc gcgtcaccac       840
gcaccgcatc gagattggca agtcggctga ggaaacggcc aaaagcatcg tcagctcttt       900
tgggggcgtc gagccagccg tgaccctgga gtgcaccggt gtggagagca gcattgcagc       960
ggccatctgg gccagcaagt ttggaggaaa ggtctttgtg atcggcgtcg gcaagaatga      1020
aatcagcatt cccttatga gggccagtgt acgcgaggtc gatatccagc tgcagtatcg      1080
ctacagcaac acctggcctc gtgccatccg gctcatcgag agcggtgtca tcgatctatc      1140
caaatttgtg acgcatcgct tcccgctgga ggatgccgtc aaggcatttg agacgtcagc      1200
agatcccaag agcggcgcca ttaaggtcat gattcagagc ctggattgag agtgaggtgc      1260
taccaggtag aggtagataa tagatagatg atgaagatgg aaagactgcg ggcgcaagaa      1320
tcgggcggat agggagttgg ctgtaatggt ttgcaaagca t                          1361
```

<210> SEQ ID NO 2
<211> LENGTH: 923
<212> TYPE: DNA
<213> ORGANISM: L-xylulose reductase

<400> SEQUENCE: 2

```
ccccatcctt tgcatcgccc atcatgcctc agcctgtccc caccgccaac agactccttg        60
atctcttcag cttgaagggc aaggtcgtcg tcgtcaccgg cgcttccggc cctcgaggca       120
tgggaatcga agctgcccgt ggctgcgccg agatgggcgc tgacctcgcc atcacctact       180
cgtctcgcaa ggagggcgcg gagaagaacc ccgaggaatt gaccaaggaa tacgcgtcga       240
aagtcaaggt gtacaaggtc aaccagagcg actacaacga tgttgagcgc tttgtgaacc       300
aggtcgtgtc tgactttggc aagatcgatg cctttattgc caacgccgga ccacagcta       360
atagcggagt tgttgacggc agcgccagcg attgggacca tgtcatccag gtcgacctga      420
```

```
gcggcaccgc atactgcgca aaggctgttg gcgcgcactt caagaagcag ggccacggct      480
cccttgtcat cacagcttca atgtccggcc acgtcgcaaa ctatccccag gaacagacct      540
catacaacgt cgccaaggcc ggttgcatcc atctggcgcg gtctctggcc aacgagtggc      600
gtgattttgc ccgcgtcaac agcatttcgc ccggttatat cgataccggc ctgtccgact      660
tcatcgacga gaagacgcaa gagctgtgga ggagcatgat ccccatggga cgaaacggcg      720
atgccaagga gctcaagggc gcgtatgtat atctggtcag cgacgctagc tcgtacacga      780
cgggagccga tattgtgatt gacggaggtt acactacacg ataaagaaat aatgtattgt      840
tagactataa tcaatgtgac gaacaagatt tgtgattaag aaaaaaaaaa aaaaaaaaa       900 aaaactcgag taattccgat aga                                              923
```

ENGINEERING FUNGI FOR THE UTILISATION OF L-ARABINOSE

Cross Reference to Related Applications

This application is for entry into the U.S. national phase under §371 for International Application No. PCT/FI02/00125 having an international filing date of Feb. 15, 2002, and from which priority is claimed under all applicable sections of Title 35 of the United States Code including, but not limited to, Sections 120, 363 and 365(c), and which in turn claims priority under 35 USC 119(e) to Finnish Patent Application No. 20010308 filed on Feb. 16, 2001.

FIELD OF THE INVENTION

The present invention relates to a genetically modified fungus and its use for the production of useful products such as ethanol, lactic acid, xylitol and the like from materials containing the pentose sugar L-arabinose.

BACKGROUND OF THE INVENTION

L-arabinose is a major constituent of plant material. L-arabinose fermentation is therefore also of potential biotechnological interest.

Fungi that can use L-arabinose and D-xylose are not necessarily good for industrial use. Many pentose utilising yeast species for example have a low ethanol tolerance, which makes them unsuitable for ethanol production. One approach would be to improve the industrial properties of these organisms. Another is to give a suitable organism the ability to use L-arabinose and D-xylose. There are pathways for D-xylose and L-arabinose, which are known to be active in bacteria. For D-xylose catabolism it is a xylose isomerase, which converts D-xylose to D-xylulose and a xylulokinase to make D-xylulose 5-phosphate. For L-arabinose catabolism the pathway consists of an isomerase, a kinase and an epimerase which convert L-arabinitol to L-ribulose, L-ribulose 5-phosphate and D-xylulose 5-phosphate, with D-xylulose 5-phosphate being an intermediate of the pentose phosphate pathway (Stryer, 1988). It has been tried to overexpress this bacterial pathway in the yeast *S. cerevisiae*, but it was not functional. The three enzymes of the L-arabinose pathway were expressed and shown to be active. However no growth on L-arabinose as a sole carbon source was reported (Sedlak and Ho, 2001). Also the expression of xylose isomerase in a fungal host was not successful (Sarthy et al. 1987, Chan et al. 1989, Kristo et al. 1989, Moes et al 1996, Schründer et al. 1996). The reason for this is not clear. There might be a species barrier, which prevents these bacterial isomerases from working in fungi. It can also be metabolic imbalances in the host, which are solved by an unknown mechanism in the donor.

There is also a hypothetical eukaryotic, i.e. fungal pathway, where L-arabinose is also converted to D-xylulose 5-phosphate, but by a different pathway (see FIG. 1). This pathway has been suggested to use 2 reductases, 2 dehydrogenases and a kikinase as shown (Chiang and Knight, 1961, Witteveen et al., 1989). While the genes of the bacterial pathway have been known for decades, very little is known about this hypothetical fungal pathway.

A fungal pathway for L-arabinose utilisation was described by Chiang and Knight (1961) for *Penicillium chrysogenum* and by Witteveen et al. (1989) for *Aspergillus niger*. It consists of an NADPH-linked reductase, which forms L-arabinitol, an NAD-linked dehydrogenase which forms L-xylulose, an NADPH-linked reductase which forms xylitol, an NAD-linked dehydrogenase which forms D-xylulose and a xylulokinase. The final product is D-xylulose 5-phosphate as in the bacterial L-arabinose pathway (see FIG. 1). This pathway was described only for filamentous fungi, but there are indications that it may also occur in yeast. Shi et al. (2000) described a mutant of *Pichia stipitis* which was unable to grow on L-arabinose. Over-expression of the NAD-linked xylitol dehydrogenase could restore the growth on L-arabinitol indicating that xylitol may be an intermediate in the L-arabinose pathway. Also yeast strains, which had L-arabinose as a sole carbon source, produced L-arabinitol and small amounts of xylitol (Dien et al., 1996), indicating that yeast might use this pathway. The capability of L-arabinose fermentation is not a common feature of yeast. Many yeast species mainly accumulate the L-arabinitol formed from L-arabinose (McMillan and Boynton 1994). Only recently yeast species were identified which were capable of L-arabinose fermentation (Dien et al., 1996).

The hypothetical fungal L-arabinose pathway has similarities to the fungal D-xylose pathway. In both pathways the pentose sugar goes through reduction and oxidation reactions where the reductions are NADPH-linked and the oxidations NAD-linked. D-xylose goes through one pair of reduction and oxidation reaction and L-arabinose goes through two pairs. The process is redox neutral but different redox cofactors, i.e. NADPH and NAD are used, which have to be separately regenerated in other metabolic pathways. In the D-xylose pathway an NADPH-linked reductase converts D-xylose into xylitol, which is then converted to D-xylulose by an NAD-linked de-hydrogenase and to D-xylulose 5-phosphate by xylulokinase. The enzymes of the D-xylose pathway can all be used in the L-arabinose pathway. The first enzyme in both pathways is an aldose reductase (EC 1.1.1.21). The corresponding enzymes in *Saccharomyces cerevisiae* (Kuhn et al. 1995) and *Pichia stipitis* (Verduyn, 1985) have been characterised. They are unspecific and can use either L-arabinose or D-xylose with approximately the same rate to produce L-arabinitol or xylitol respectively. Genes coding for this enzyme are known e.g. for *Pichia stipitis* (Amore et al., 1991), *Saccharomyces cerevisiae* (Kuhn et al., 1995, Richard et al. 1999), *Candida tenius* (Hacker et al., 1999), *Kluyveromyces lactis* (Billard et al., 1995) and *Pachysolen tannophilus* (Bolen et al., 1996).

The xylitol dehydrogenase (also known as D-xylulose reductase EC 1.1.1.9) and xylulokinase EC 2.7.1.17 are the same in the D-xylose and L-arabinose pathway of fungi. Genes for the D-xylulose reductase are known from *Pichia stipitis* (Kötter et al. 1990) *Saccharomyces cerevisiae* (Richard et al. 1999) and *Tricoderma reesei* (Wang et al. 1998). The gene for a fungal xylulokinase is only known for *Saccharomyces cerevisiae* (Ho and Chang, 1998)

Genes coding for L-arabinitol 4-dehydrogenase (EC1.1.1.12) or L-xylulose reductase (EC 1.1.1.10) are not known.

The invention aims to be able to express the pathway for L-arabinose utilisation in fungi. The hypothetical fungal pathway expressed in *Saccharomyces cerevisiae* would result in a strain, which can ferment nearly all sugars from forestry and agricultural waste to ethanol.

SUMMARY OF THE INVENTION

According to the invention, the inability of a fungus to utilize L-arabinose efficiently is solved by a genetic modification of the fungus, which is characterised in that the fungus is transformed with a gene for L-arabinitol 4-dehydrogenase or a gene for L-xylulose reductase or both such genes.

According to the present invention, a fungus is transformed with all or some of the genes coding for the enzymes of the L-arabinose pathway, i.e. aldose reductase, L-arabinitol 4-dehydrogenase, L-xylulose reductase, D-xylulose reductase and xylulokinase. The resulting fungus is then able to utilise L-arabinose. We disclose genes for L-arabinitol dehydrogenase and L-xylulose reductase. We disclose that when a fungus as S. cerevisiae that is unable to utilise L-arabinose is transformed with genes for aldose reductase, L-arabinitol 4-dehydrogenase, L-xylulose reductase, D-xylulose reductase and xylulokinase, it becomes able to utilise L-arabinose. We also disclose that when a fungus, such as genetically engineered S. cerevisiae, that can use D-xylose but not L-arabinose is transformed with genes for L-arabinitol 4-dehydrogenase and L-xylulose reductase it can utilise L-arabinose.

By the term utilisation is meant here that the organism can use L-arabinose as a carbon source or as an energy source or that it can convert L-arabinose into another compound that is a useful substance.

BRIEF DESCRIPTION OF THE DRAWINGS

FIG. 1. The hypothetical fungal and the bacterial pathway for L-arabinose utilisation.

FIG. 2. L-arabinitol 4-dehydrogenase gene sequence (SEQ ID NO. 1): The sequence of the genomic DNA was combined with the cDNA sequences of the N-terminal and C-terminal region. The intron sequence is from nucleotide 247 to 315. The protein is encoded from nucleotide 47 to 1246 (SEQ ID NO: 17).

FIG. 3. Sequence of the cDNA clone and protein sequence for the L-xylulose reductase (SEQ ID No. 2). The protein is encoded from nucleotide 24 to 821 (SEQ ID NO: 18).

DETAILED DESCRIPTION OF THE INVENTION

Figure 4:
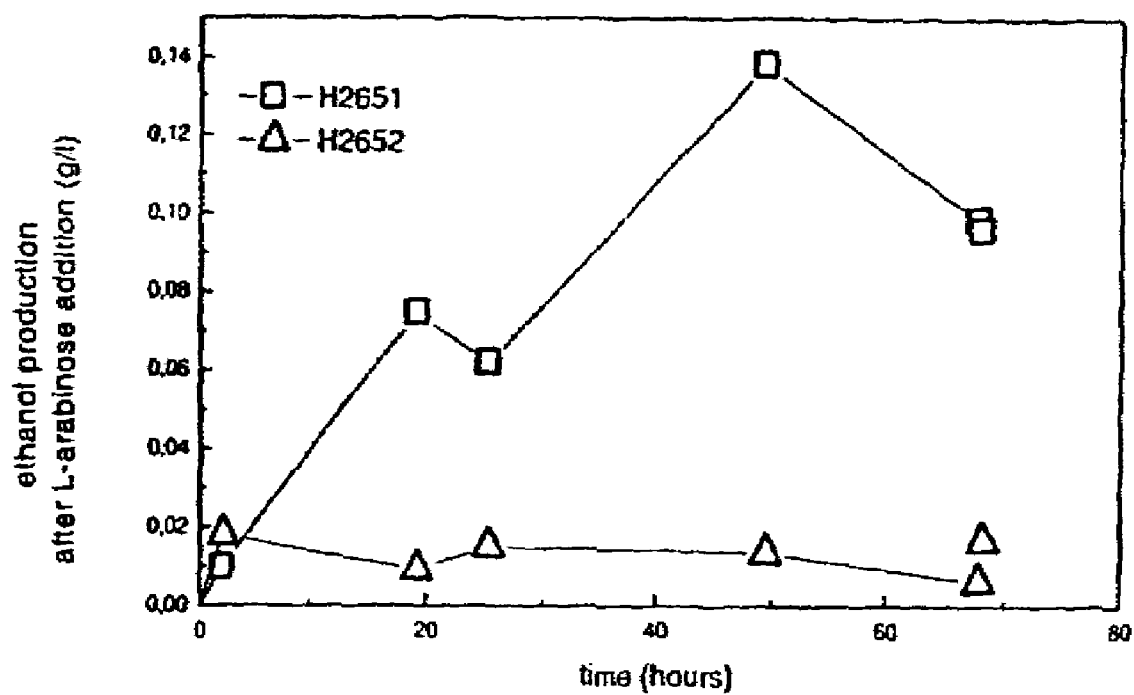
FIG. 4. Ethanol production from L-arabinose using a genetically modified fungus according to the invention (strain H2651) compared to a control strain (H2652).

The central teaching of this invention is to demonstrate how a fungal microorganism can be genetically engineered to utilise L-arabinose. By utilization we mean that the organism can use L-arabinose as a carbon source or as an energy source or that it can convert L-arabinose into another compound that is a useful substance. Some fungi can naturally utilise L-arabinose, others cannot. It can be desirable to transfer the capacity of utilising L-arabinose to a organism lacking the capacity of L-arabinose utilisation but with other desired features, such as the ability to tolerate industrial conditions or to produce particular useful products, such as ethanol or lactic acid or xylitol. In order to transfer the capacity of L-arabinose utilisation by means of genetic engineering it is essential to know all the genes of a set of enzymes that can function together in a host cell to convert L-arabinose into a derivative, e.g. D-xylulose 5-phosphate, that the host can catabolise and so produce useful products. This set of enzymes can then be completed in a particular host by transforming that host with the gene or genes encoding the missing enzyme or enzymes.

One example is to genetically engineer S. cerevisiae to utilise L-arabinose. S. cerevisiae is a good ethanol producer but lacks the capacity for L-arabinose utilisation. Other examples are organisms with a useful feature but lacking at least part of a functional L-arabinose pathway.

An L-arabinose pathway believed to function in fungi is shown in the FIG. 1. Genes coding for the aldose reductase (EC 1.1.1.21), the D-xylulose reductase (EC 1.1.1.9) and xylulokinase (EC 2.7.1.17) are known. In order to construct a strain that can use L-arabinose by this hypothetical pathway, two additional genes would be required, i.e. genes for L-arabinitol 4-dehydrogenase (EC 1.1.1.12) and for L-xylulose reductase (EC 1.1.1.10).

L-arabinitol 4dehydrogenase: An L-arabinitol 4-dehydrogenase was described for Penicillium chrysogenum and Aspergillus niger by Chiang and Knight (1960) and Witteveen et al (1989) respectively. This enzyme converts L-arabinitol and NAD to L-xylulose and NADH. It was also reported to have activity with NAD and adonitol (ribitol) and NAD and xylitol (Chiang and Knight, 1960).

L-xylulose reductase: The L-xylulose reductase (EC 1.1.1.10) converts xylitol and NADP to L-xylulose and NADPH. Another enzyme, which has been reported to catalyse the same reaction, is the D-iditol 2-dehydrogenase (EC 1.1.1.15) (Shaw, 1956).

L-xylulose reductase was found in Erwinia uredovora (Doten et al, 1985), Aspergillus niger (Witteveen et al. 1994) and guinea pig (Hickman and Ashwell, 1959). A preparation from pigeon liver is commercially available (Sigma-Aldrich). A single subunit of the enzyme from Aspergillus niger has a molecular weight 32 kDa, the native enzyme an estimated weight of 250 kDa (Witteveen et al. 1994).

However, the amino acid sequences and the encoding genes are not known for any L-arabinitol dehydrogenase or L-xylulose reductase. We now disclose such genes. We also disclose that transforming these genes into a fungus that cannot utilise L-arabinose but can utilise xylose confers the ability to utilise L-arabinose upon the transformed fungus.

To identify the genes for L-arabinitol 4-dehydrogenase or L-xylulose reductase different approaches are possible and a person knowledgeable in the art might use different approaches. One approach is to purify the protein with the corresponding activity and use information about this protein to clone the corresponding gene. This can include the proolytic digestion of the purified protein, amino acid sequencing of the proteolytic digests and cloning a part of the gene by PCR with primers derived from the amino acid sequence. The rest of the DNA sequence can then be obtained in various ways. One way is from a cDNA library by PCR using primers from the library vector and the known part of the gene. Once the complete sequence is known the gene can be amplified from the cDNA library and cloned into an expression vector and expressed in an heterologous host. This is a useful strategy if screening strategies or strategies based on homology between sequences are not suitable.

Another approach to clone a gene is to screen a DNA library. This is especially a good and fast procedure, when overexpression of a single gene causes a phenotype that is easy to detect. Now that we have disclosed that transformation of a xylose-utilising fungus with genes encoding L-arabinitol dehydrogenase and L-xylulose reductase confers the ability to grow in L-arabinose, another strategy to find the genes for L-arabinitol 4-dehydrogenase and L-xylulose reductase is the following: One of the two enzymes is purified and the corresponding gene is cloned. Now all the genes of the pathway, except one, are known. In this situation a screening strategy is suitable to find the last gene of the pathway. A strain with all the genes of the pathway except one can be constructed, transformed with a DNA library, and screened for growth on L-arabinose. In this strategy one can first purify the L-arabinitol 4-dehydrogenase and then screen for the L-xylulose reductase or first purify the L-xylulose reductase and then screen for the L-arabinitol 4-dehydrogenase.

There are other ways and possibilities to clone these genes:

One can purify both enzymes and find the corresponding genes.

One can screen a DNA library or a combination of two DNA libraries to find both genes at once.

One can use other screens to find the individual genes.

One could screen for example for growth on L-xylulose to find the L-xylulose reductase and then for growth on L-arabinose or L-arabinitol to screen for L-arabinitol 4-dehydrogenase.

Other possible screens could make use of the cofactor requirements, e.g. in a screening condition which is lethal because of NADPH depletion one could screen for a L-xylulose reductase in the presence of xylitol.

One can screen existing databanks for genes with homology to genes from related protein families and test whether they encode the desired enzyme activity. Now that we have disclosed sequences for genes encoding L-arabinitol-4-dehydrogenase (SEQ ID NO 1) and L-xylulose reductase (SEQ ID NO 2), it is easy for a person skilled in the art to screen data banks for genes homologous to SEQ ID NOs 1 and 2. Homologous genes can also be readily found by physical screening of DNA libraries using probes based on SEQ ID NOs 1 and 2. Suitable DNA libraries include DNA isolated from fungi and other microbes able to utilise L-arabinose or L-xylulose.

For a person skilled in the art there are different ways to identify the gene, which codes for a protein with the desired enzyme activity. The methods described here illustrate our invention, but any other method known in the art may be used Once all the genes of the L-arabinose pathway are identified, this pathway can be introduced to a new host organism, which is lacking this pathway. It is not always necessary to introduce all the genes. It might be that the host organism has already part of the pathway. For example a fungus that can utilise D-xylose might only require the enzymes that convert L-arabinitol to xylitol. Expression of L-arabinitol 4-dehydrogenase and L-xylulose reductase would then be sufficient to complete the L-arabinose pathway. Enzyme assays have been described for all the steps of the fungal arabinose pathway (Witteveen et al. 1989) and these can be used if necessary to help identify the missing or inefficient steps in a particular host.

The L-arabinose pathway can be introduced to *S. cerevisiae* to generate a strain, which is a good ethanol producer and can utilise the pentoses L-arabinose and D-xylose. In such a strain the most abundant hexose and pentose sugars can be fermented to ethanol.

In Examples 3 and 5 the genes were cloned into a genetically engineered laboratory strain of *S. cerevisiae*. The same approach can be used with an industrial strain of *S. cerevisiae*, e.g. a brewer's, distiller's or baker's yeast. Industrial yeasts have process advantages such as high ethanol tolerance, tolerance of other industrial stresses and rapid fermentation. They are normally polyploid and their genetic engineering is more difficult compared to laboratory strains, but methods for their engineering are known in the art (see, e.g., Blomqvist et al, 1991; Henderson et al. 1985). Other yeasts unable or inefficient to utilise L-arabinose could be used as hosts, e.g. *Schizosaccaromyces pombe* or *Pichia* spp., *Candida* spp., *Pachysolen* spp., *Schwanniomyces* spp., *Arxula*, spp., *Trichosporon* spp., *Hansenula* spp. or *Yarrowia* spp. Potential hosts also include filamentous fungi such as *Aspergillus* species, *Trichoderma* species, *Neurospora* species, *Fusarium* species, *Penicillium* species, *Humicola* species, *Tolypocladium geodes*, *Trichoderma reesei* (*Hypocrea jecorina*), *Mucor* species, *Trichoderma longibrachiatum, Aspergillits nidulans*, *Aspergillus niger* or *Aspergillus awamori*. But our invention is not restricted to yeasts and other fungi. The genes encoding L-arabinitol 4-dehydrogenase and/or L-xylulose reductase can be expressed in any organism such as bacteria, plants or higher eukaryotes unable to use or inefficient in using L-arabinose by applying the genetic tools suitable and known in the art for that particular organism.

In Examples 3 and 5 we used a TPI promoter from *S. cerevisiae* for the expression of L-arabinitol 4-dehydrogenase and the PGK promoter from *S. cerevisiae* for the expression of L-xylulose reductase. Both promoters are considered strong and constitutive. Other promoters, which are stronger or less strong, can be used. It is also not necessary to use a constitutive promoter. Inducible or repressible promoters can be used, and may have advantages, for example if a sequential fermentation of different sugars is desired.

In our example we used two plasmids for the two genes L-arabinitol 4-dehydrogenase and L-xylulose reductase. Each plasmid contained a different selection marker. These genes can also be expressed from a single plasmid with or without a selection marker or they can be integrated into the chromosom. The selection markers were used to find successful transformations more easily and to stabilise the genetic construct. The yeast strain was transformed successively with the different genes and the transformation to *S. cerevisile* was performed with the lithium acetate procedure (Gietz et al. 1992). This is only one method to accomplish the desired genetic construct. All the necessary genes can be transformed simultaneously or in succession. Other transformation procedures are known in the art, some being preferred for a particular host, and they can be used to achieve our invention.

In Examples 2 and 4 are disclosed the nucleotide sequences (SEQ ID NOs 1 and 2, respectively) of *T reesei* genes encoding L-arabinitol dehydrogenase and L-xylulose reductase. These are suitable genes for practising our invention as is disclosed in Examples 5 and 6. It is well known that genes from different organisms encoding enzymes with the same catalytic activity have sequence similarities and these similarities can be exploited in many ways by those skilled in the art to clone other genes from other organisms with the same catalytic activity. Such genes are also suitable to practise our invention. It is also well known that many small variations in the nucleotide sequence of a gene do not significantly change the catalytic properties of the encoded protein. For example, many changes in nucleotide sequence do not change the amino acid sequence of the encoded protein, whereas many changes in amino acid sequence do not change the functional properties of a protein, in particular they do not prevent an enzyme from carrying out its catalytic function. We call such variations in the nucleotide sequence of DNA molecules "functionally equivalent variations" because they do not significantly change the function of the gene to encode a protein with a particular function, e.g. catalysing a particular reaction. DNA molecules that are functionally equivalent variations of the molecules defined by SEQ ID NOs 1 and 2 can be used to practise our invention.

Sometimes organisms contain genes that are not expressed under conditions that are useful in biotechnological applications. For example, although it was once generally believed that *S. cerevisiae* cannot utilise xylose and it was therefore expected that *S. cerevisae* did not contain genes encoding enzymes that would enable it to use xylose it has nevertheless been shown that *S. cerevisiae* does contain such genes (Richard et al 1999). However, these genes are not usually expressed adequately. Thus, another aspect of our invention is to identify genes for L-arabinitol 4-dehydrogenase or L-xylulose reductase or both in a host organism itself and to cause these genes to be expressed in that same organism under conditions that are convenient for a biotechnological process, such as ethanolic fermentation of L-arabinose-containing biomass. We disclose a method of identifying candidates for such normally unexpressed genes, which is to search for similarity to SEQ ID NOs 1 and 2. A candidate gene can then be cloned in an expression vector and expressed in a suitable host and cell-free extracts of the host tested for appropriate catalytic activity as described in Examples 1 and 6. When the normally unexpressed or inadequately expressed gene has been confirmed to encode the desired enzyme, the gene can then be cloned back into the original organism but with a new promoter that causes the gene to be expressed under appropriate biotechnological conditions. This can also be achieved by genetically engineering the promoter of the gene in the intact organism.

In yet another aspect of the invention the genes encoding L-arabinitol dehydrogenase and L-xylulose reductase from a fungus, including, fungi such as filamentous fungi that can have the ability to utilise L-arabinose, can now be easily identified by similarity to SEQ ID NOs 1 and 2. These genes can then be modified for example by changing their promoters to stronger promoters or promoters with different properties so as to enhance the organism's ability to utilise L-arabinose.

One embodiment of this aspect is to modify these genes (and possibly also the well known gene encoding D-xylulose reductase) to create a fungus with an enhanced capacity to produce the valuable sugar alcohols, L-arabinitol and xylitol, the latter being a useful sweetener. For example, a fungus containing aldose reductase but lacking L-arabinitol 4-dehydrogenase will convert L-arabinose to L-arabinitol and can now be created by the steps of (1) transforming the fungus with the gene for aldose reductase if it lacks this enzyme and (2) deleting or disrupting the gene for L-arabinitol 4-dehydrogenase by well known methods that utilise the sequence we disclose for this gene (SEQ ID NO 1). Similarly a fungus that contains all the enzymes of the fungal pathway for converting L-arabinose to xylitol but lacks D-xylulose reductase will convert L-arabinose into xylitol and can now be created using the information we disclose in SEQ ID NOs 1 and 2 together with information about genes for D-xylulose reductase that is already known.

A fungus may not naturally have the enzymes needed for lactic acid production, or it may produce lactic acid inefficiently. In these cases expression of the gene encoding lactate dehydrogenase (LDH) enzyme can be increased or improved in the fungus, and a fungus can then produce lactic acid more efficiently (e.g. WO 99/14335). Similarly, using methods known in the art, a fungus modified to use arabinose more efficiently as described in this invention can be further modified to produce lactic acid. As well as ethanol, lactate and sugar alcohols such as arabinitol and xylitol, other useful products can be obtained from the L-arabinose-utilizing fungi of the present invention. These fungi convert L-arabinose via the arabinose pathway to xylulose-5-phosphate, which is an intermediate of the pentose phosphate pathway. Thus, derivatives of the pentose phosphate pathway, such as aromatic aminoacids, can also be produced as well as other substances derived from pyruvate, the common precursor of lactate and ethanol.

The transformed fungus of the invention may be used to produce ethanol from L-arabinose. A host fungus is transformed with genes for L-arabinitol 4-dehydrogenase, L-xylulose reductase or both. The host can be any fungus that has no or only a limited ability to use L-arabinose but is able to ferment D-xylose. For example it can be a *Saccharomyces cerevisiae* strain that has been transformed with genes enabling it to ferment D-xylose. The genes for L-arabinitol 4-dehydrogenase and L-xylulose reductase can be obtained from *T. reesei*, as described in Examples 2 and 4, but other genes encoding enzymes with these catalytic activities can also be used. Such genes are now easily found, for example from microorganisms able to use L-arabinose, because the sequences disclosed as SEQ ID Nos 1 and 2 can be exploited in various ways well known in the art to clone similar genes. The methods used to transform the host fungus and to select transformants can be the same as those used in Examples 3 and 5, but other methods known in the art can be used successfully to provide a transformed fungus according to our invention.

The transformed fungus is then used to ferment a carbon source such as biomass comprising agricultural or forestry products and waste products containing L-arabinose and possibly also other pentoses or other fermentable sugars. The preparation of the carbon source for fermentation and the fermentation conditions can be the same as those that would be used to ferment the same carbon source using the host fungus. However, the transformed fungus according to the invention consumes more L-arabinose than does the host fungus and produces a higher yield of ethanol on total carbohydrate than does the host fungus. This is shown in Example 7. It is well known that fermentation conditions, including preparation of carbon source, addition of co-substrates and other nutrients, and fermentation temperature, agitation, gas supply, nitrogen supply, pH control, amount of fermenting organism added, can be optimised according to the nature of the raw material being fermented and the fermenting microorganism. Therefore the improved performance of the transformed fungus compared to the host fungus can be further improved by optimising the fermentation conditions according to well-established process engineering procedures.

Use of a transformed fungus according to the invention to produce ethanol from carbon sources containing L-arabinose and other fermentable sugars has several industrial advantages. These include a higher yield of ethanol per ton of carbon source and a higher concentration of ethanol in the fermented material, both of which contribute to lowering the costs of producing, for example, distilled ethanol for use as fuel. Further, the polution load in waste materials from the fermentation is lowered because the L-arabinose content is lowered, so creating a cleaner process.

Lignocellulosic raw materials are very abundant in nature and offer both renewable and cheap carbohydrate sources for microbial processing. Arabinose-containing raw materials are e.g. various pectins and hemicellulosics (such as xylans) which contain mixtures of hexoses and pentoses (xylose, arabinose). Useful raw materials include by-products from paper and pulp industry such as spent liquor and wood hydrolysates, and agricultural by-products such as sugar bagasse, corn cobs, corn fiber, oat, wheat, barley and rice hulls and straw and hydrolysates thereof. Also arabanane or galacturonic acid containing polymeric materials can be utilised.

EXAMPLES

Example 1

Purification and amino acid sequencing of the L-arabinitol 4-dehydrogenase:

*Tricoderma reesei* (Rut C-30) was grown in a medium containing 40 g/l L-arabinose, 2 g/l proteose peptone, 15 g/l $KH_2PO_4$, 5 g/l $(NH_4)_2SO_4$, 0.6 g/l $Mg_2SO_4 \times 7\ H_2O$, 0.8 g/l CaCl$_2$×2H$_2$O and trace elements (Mandels and Weber, 1969) at 28 C, pH 4.0 and 30% dissolved oxygen in a fermenter (Chepmap CF2000). The fermentation was stopped when the L-arabinose was about 10 g/l. The cells were harvested with a plastic mesh sieve and washed with 10 mM sodium phosphate pH 7. 500 g of the biomass was frozen in liquid nitrogen in 100 g aliquots. After thawing and sonifying with a tip sonifyer, DTT was added to a final concentration of 5 mM and the suspension centrifuged (Sorvall SS34, 40 min, 20 000 rpm). The supernatant was dialysed overnight against a 10 fold volume of buffer A: 10 mM sodium phosphate pH 7, 5 mM DTT. The retentate was then centrifuged (Sorvall SS34, 40 min, 20 000 rpm). All steps were performed at 4 ° C. The crude extract had a protein content of 7 g/l and an L-arabinitol dehydrogenase activity of 0.7 nkat per mg of extracted protein. 500 ml of this crude extract was loaded to a column with 200 ml DEAE and eluted with a linear gradient from buffer A to buffer A supplemented with 100 mM NaCl. The highest activity (16 nkat/mg, 5 mg/ml protein) eluted at about 80 mM NaCl.

The L-arabinitol 4-dehydrogenase activity was measured by adding the enzyme preparation to a buffer containing 100 mM Tris HCl pH 9.0, 0.5 mM MgCl$_2$, 2 mM NAD. The reaction was then started by adding L-arabinitol (or other sugars if specified) to a final concentration of 10 mM. The activity was calculated from the changes in NADH absorbance at 340 nm. All enzyme assays were done at 37 ° C. in a Cobas Mira automated analyser (Roche). In the reverse reaction the activity was measured by adding the enzyme preparation to a buffer containing 200 mM NaPO$_4$ pH 7.0, 0.5 mM MgCl$_2$, 200 µM NADH and 2 mM L-xylulose. The activity was calculated from the changes in NADH absorbance at 340 nm.

The partially purified enzyme was tested for activity with other sugars. No activity was found with D-arabinitol. Activity was found with L-arabinitol and adonitol (ribitol). The activity with ribitol was about 80% of the activity found with L-arabinitol. No activity with either sugar was found when NADP was used as a co-substrate.

In the reversible reaction with L-xylulose and NADH an activity of 0.8 nkat/mg was found with 2 mM L-xylulose at pH 7.0 compared to 6.4 nkat/mg with 10 mM L-arabinitol and 5 nkat/mg with 10 mM adonitol (ribitol).

600 µl of the fraction with the highest activity after the DEAE column was then run on a native PAGE (12% acrylamide, BioRad). The gel was then stained in a Zymogram staining solution containing: 200 mM TrisHCl pH 9.0, 100 mM L-arabinitol, 0.25 mM nitroblue tetrazolium, 0.06 mM phenazine metosulfate, 1.5 mM NAD.

The only band which appeared in the staining was cut out and eluted by over-night incubation in 2 ml 100 mM TrisCl pH 9.0, 0.1% SDS. It was then concentrated to about 80 µl with Centricon (Amicon).

This gave an almost pure enzyme preparation with the major band in SDS PAGE at about 38 kDa. This protein was then used for amino acid sequencing of the proteolytic digests. The results of this sequencing were the following:

Internal peptide sequences of the purified L-arabinitol 4 dehydrogenase:

```
                                              (SEQ ID NO: 3)
1: A T G A A I S V K P N I G V F T N P K

2: Y S N T W P R                              (SEQ ID NO: 4)

3: A F E T S A D P K                          (SEQ ID NO: 5)

4: H D L W I S E A E P                        (SEQ ID NO: 6)
```

Example 2

Cloning of the L-arabinitol 4-dehydrogenase:

Cloning a gene fragment by using the internal amino acid sequences:

The internal peptide sequences were used to design degenerative primers for PCR. The template in the first approach was genomic DNA from *Tricoderma reesei*. A sense DNA sequence corresponding to the amino acid fragment ATGAAISVKPNIGVFTNPK (SEQ ID NO: 3) (primer 5384: ARCCIAAYATHGGIGTITTYACIAAYCC (SEQ ID NO: 7)) and an anti-sense DNA sequence corresponding to the amino acid fragment AFETSADPK (SEQ ID NO: 5) (primer 5285:GGRTCIGCIGAIGTYTCRAAIGC (SEQ ID NO: 8)) were used. The PCR conditions were: denaturation 30 s, 96 ° C., annealing 30 s, first 2 times 37° C. and then 27 times 42° C., extention 2 mm at 72° C., final extention 5 mm 72° C. This procedure gave a PCR product of about 1 kb. The resulting fragment of about 1 kb was then cloned to a TOPO vector (Invitrogen).

This construct was then used for sequencing.

The sequence of the PCR product coded also for the remaining two peptide sequences (see FIG. 2).

Cloning the N and C terminus from a cDNA library:

A cDNA library in a yeast expression vector (Margolles-Clark et al. 1996) was used to clone the residual parts of the gene. In this expression vector the cDNA is located between a PGK promoter and terminator. To clone the part of the gene, which corresponds to the N-terminus of the protein a PCR reaction was carried out with the cDNA library as a template and one primer in the PGR promoter region and an antisense primer from the gene fragment of the L-arabinitol 4-dehydrogenase.

Primer of the PGK promoter region: (primer 4196: TCAAGTTCTTAGATGCTT (SEQ ID NO: 9)).

Antisense primer of the gene fragment: (primer 5431: CCTTTCCTCCAAACTTGCTGG (SEQ ID NO: 10)).

The part of the gene, which corresponds to the C-terminus of the protein, was cloned in a similar way with primers from the gene fragment and an antisence primer from the PGK terminator.

Antisense primer of the PGK terminator region: (primer 3900: TAGCGTAAAGGATGGGG SEQ ID NO: 11)).

Primer of the gene fragment: (primer 5430: CTGCATTGGGCCCATGAT (SEQ ID NO: 12)).

The PCR conditions were as described above except the annealing was 30 times at 50° C.

The N terminus gave a PCR product of about 0.8 kb; the C terminus gave a PCR product of about 0.9 kb. The PCR products were cloned to TOPO vectors and the resulting vectors used for sequencing.

With the information of the C-terminus and the N-terminus the open reading frame was then cloned by PCR from the cDNA library. The primer for the N-terminus contained an additional EcoRI restriction site (primer 5526: AGAATTCACCATGTCGCCTTCCGCAGTC (SEQ ID NO: 13)). The primer for the C-terminus contained an additional with BamHI restriction site (primer 5468: ACGGATCCTCTACCTGGTAGCACCTCA (SEQ ID NO: 14)). The annealing in the PCR reaction was 30 times 60.5° C., otherwise the conditions were as described above. This gave a fragment of 1.1 kb, which was then cloned to a TOPO vector and used for sequencing.

Comparing the sequences derived from genomic DNA and cDNA reveals an intron of 69 base pares (see FIG. 2).

The open reading frame codes for a protein with 377 amino acids and a calculated molecular weight of 39806 g/mol.

Example 3

Expression of L-arabinitol 4-dehydrogenase in *S. cerevisiae*:

From the TOPO vector the 1.1 kb EcoRI, BamHI fragment was ligated into the corresponding sites of the pYX242 vector (R&D Systems). The pYX242 is a multi-copy yeast expression vector with a yeast TPI promoter and LEU2 for selection. This plasmid was then transformed to the *S. cerevisiae* strain CEN.PK2 (VW1b). The recombinant yeast cells were grown on selective medium. The intracellular proteins were then extracted from the yeast cells by vortexing with glass beads. The extract was then analysed for L-arabinitol dehydrogenase activity. We found an L-arabinitol 4-dehydrogenase activity of 0.2 to 0.3 nkat per mg of extracted protein.

Example 4

Screening for the L-xylulose reductase:

To screen for an L-xylulose reductase a *S. cerevisiae* strain was used which contained the genes xylose reductase (aldose reductase EC1.1.1.21), L-arabinitol-4-dehydrogenase (EC 1.1.1.12), D-xylulose reductase (EC 1.1.1.9) and xylulokinase (EC 2.7.1.17). The aldose reductase, D-xylulose reductase and xylulokinase were integrated. This strain was constructed so that uracil and leucine could still be used for selection. The plasmid from example 3 with the L-arabinitol 4-dehydrogenase on a multicopy plasmid, was transformed to the strain with the integrated aldose reductase, D-xylulose reductase and xylulokinase. In this strain the uracil auxotrophy was still left for selection. A cDNA library from *T. reesei* in a yeast expression vector with uracil marker (Margolles-Clark et al. 1996) was then transformed to this strain and screened for growth on L-arabinose. For screening the transformants were first grown on glucose plates with selection. About 750 000 transformants were then replica plated to selective plates with 5% L-arabinose as a sole carbon source. Colonies, which appeared after 2 to 3 weeks, were streaked again on L-arabinose. The resulting colonies were then grown on glucose and the plasmids rescued. The plasmids were transformed to *E. coli* cells. Since both plasmids, the plasmid with the L-arabinitol 4-dehydrogenase and the plasmid from the cDNA library, contained only ampicillin resistance, we used colony PCR to identify the *E. coli* with the cDNA library plasmid. For the colony PCR we used primers of the PGK promoter and terminator region. From 4 independent clones which appeared in the L-arabinose screening a PCR product of 0.9 kb was obtained. The corresponding plasmids were then sequenced. The sequence of the cDNA is in the FIG. 3. The open reading frame codes for a protein with 266 amino acids and a calculated molecular weight of 28,428 Da.

Example 5

Expression of the L-xylulose reductase:

The expression vector with the L-xylulose reductase obtained in example 4 was used. It was retransformed to the strain containing the genes xylose reductase (aldose reductase EC1.1.1.21), L-arabinitol-4-dehydrogenase (EC 1.1.1.12), D-xylulose reductase (EC 1.1.1.9) and xylulokinase (EC 2.7.1.17) which was also used in the example 4. As a control the empty vector cloning vector pAJ401 was transformed instead of the vector with the L-xylulose reductase. Transformants were first grown on D-glucose plates and then streaked on plates with 5% L-arabinose as a sole carbon source. The plates contained a carbon source and selective medium leaving out uracil and leucine as required for selection (Sherman et al. 1983). On the L-arabinose plates colonies appeared after 2 to 4 weeks with the strains with L-xylulose reductase, no colonies appeared in the control.

Example 6

Expression of the L-xylulose reductase under TPI promoter:

The L-xylulose reductase was cloned by PCR, using the vector from example 5 as a template. The primers were (LXR-start EcoRI: GCCGAATTCATCATGCCTCAGCCTGTC-CCCACCGCC (SEQ ID NO: 15)) and (LXR-stop HindIII: CGCCAAGCTTTTATCGTGTAGTGTAAC-CTCCGTCAATCAC (SEQ ID NO: 16)). The conditions were as in Example 2 except that the annealing temperature was 63° C. The PCR product was digested with EcoRI and HindIII. The vector pXY212 (R&D Systems) which is a yeast expression vector with TPI promoter and contains the URA3 gene for selection was digested with EcoRI and HindIII. The PCR product was then ligated to the expression vector. The resulting vector was then transformed to the yeast strain CEN.PK2. The recombinant yeast cells were grown on selective medium. The intracellular proteins were then extracted from the yeast cells by vortexing with glass beads. The extract was then analysed for L-xylulose reductase activity. The activity was measured in a medium containing 100 mM TrisCl pH 9.0, 1.6 M xylitol and 2 mM $MgCl_2$. 2 mM NADP (final concentration) was added as a start reagent. The activity was calculated from the change in NADPH absorbance at 340 nm. The assay was performed at 37° C. in a Cobas Mira automated analyser (Roche). The activity was between 2 and 5 nkat per mg of extracted protein.

Example 7

L-arabinose fermentation with the recombinant yeast strains:

A yeast strain carrying all the genes of the L-arabinose pathway was constructed. For that purpose, a strain was constructed where the aldose reductase and xylitol dehydrogenase (Toivari et al. 2001) and the xylulokinase (Richard et al. 2000) were integrated into the chromosomes and the L-arabitol dehydrogenase and L-xylulose reductase were expressed from plasmids. The plasmids are described in the examples 3 and 6. The resulting strain carrying all the genes of the L-arabinose pathway was called H2651. A control strain (H2652) was constructed which was similar to the strain H2651 except that it carried the empty plasmid pYX212 instead of the lxr1 containing plasmid.

Fermentation was carried out as a batch cultivation in two separate fermentors, one containing the strain H2651, the other the strain H2652. Cells were first grown in shake flasks on selective media with glucose as a carbon source (SCD-leu-ura) to an $OD_{600}$ of approximately 8, then harvested and inoculated to the fermentors and cultivated two days on D-glucose. After two days the cells had metabolised all the ethanol produced from D-glucose. L-arabinose was then added and the fermentation switched to anaerobiosis. The $OD_{600}$ after L-arabinose inoculation of the strains H2651 and H2652 were 16.6 and 8.9 respectively. FIG. 4 shows that the strain H2651 produced more than 0.12 g/l ethanol from L-arabinose during the first 50 hours of cultivation on the L-arabinose. During the same time ethanol production by the control strain was almost not detectable.

REFERENCES

Amore, R., Kötter, P., Kuster, C., Ciriacy, M. and Hollenberg, C. P. (1991) Cloning and expression in *Saccharomyces cerevisiae* of the NAD(P)H-dependent xylose reductase-encoding gene (XYL1) from the xylose assimilating yeast *Pichia stipitis*. Gene 109, 89-97

Billard, P., Menart, S., Fleer, R. and Bolotin-Fukuhara, M. (1995) Isolation and characterisation of the gene encoding xylose reductase from *Kluyveromyces lactis*. Gene 162, 93-97.

Blomqvist, K., Suihko, M.-L., Knowles, J. and Penttilä, M. (1991) Chromosomal integration and expression of two bacterial α-acetolactate decarboxylase genes in brewer's yeast. Appl. Environ. Microbiol. 57, 2796-2803.

Bolen, P. L., Hayman, G. T. and Sheperd, H. S. (1996) Sequence and analysis of an aldose reductase gene from xylose fermenting yeast *Pachysolen tannophilus*. Yeast, 12, 1367-1375

Chan, E.-C., Ueng, P. P. and Chen, L. F. (1989) Metabolism of D-xylose in *Schizosaccharomyces pombe* cloned with a xylose isomerase gene. Appl. Micrbiol. Biotechnol. 31, 524-528

Chiang, C. and Knight, S. G. (1960) A new pathway of pentose metabolism. Biochem. Biophys. Res. Commun. 3, 554-559

Chiang, C and Knight, S. G. (1961) L-arabinose metabolism by cell free extracts of *Penicillium chrysogenum*. Biochim. Biophys. Acta 35, 454-463

Dien, B. S., Kurtzman, C. P., Saha, B. C. and Bothast, R. J. (1996) Screening for L-arabinose fermenting yeasts. Appl. Biochem. Biotechnol. 47/48, 233-242

Doten, R. C. and Mortlock, R. P. (1985) Characterisation of xylitol-utilizing mutants of *Erwinia uredovora*. J. Bacteriol. 161, 529-533

Gietz, D., St Jean, A., Woods, R. A., and Schiesti, R. A. (1992) Improved method for high efficiency transformation of intact yeast cells. Nucleic Acids Res. 20, 14125

Hacker, B., Habenicht, A., Kiess, M. and Mattes R. (1999) Xylose utilisation: cloning and characterisation of the xylose reductase from *Candida tenius*. Biol. Chem. 380, 1395-1403

Henderson, R. C. A., Cox, B. S. and Tubb, R. (1985) The transformation of brewing yeasts with a plasmid containing the gene for copper resistance. Current Genetics, 9, 133-138

Hickman, J. and Ashwell, G. (1959) A sensitive and stereospecific enzymatic assay for xylulose. J. Biol. Chem. 234, 758-761

Ho, N. W. Y. and Chang, S.-F. (1989) Cloning of yeast xylulokinase gene by complementation of *E. coli* and yeast mutations. Enzyme Microb. Technol. 11, 417-421

Kötter, P, Amore, R., Hollenberg, C. P. and Ciriacy, M. (1990) Isolation and characterisation of the *Pichia stipitis* xylitol dehydrogenase gene, XYL2, and construction of a xylulose-utilizing *Saccharomyces cerevisiae* transformant. Curr. Genet. 18, 493-500

Kristo, P., Saarelainen, R., Fagerström, R., Aho, S. and Korhola, M. (1996) Protein purification, and cloning and characterization of the cDNA and gene for xylose isomerase of barley. Eur. J. Biochem. 237, 240-246

Kuhn, A., van Zyl, C., van Tonder, A. and Prior. B. A. (1995) Purification and partial characterisation of an aldo-keto reductase from *Saccharomyces cerevisiae*. Appl. Environ. Microbiol. 61, 1580-1585

McMillan, J. D. and Boynton (1994) Arabinose utilisation by xylose fermenting yeasts and fungi. Appl. Biochem. Biotechnol. 45/46, 596-584

Mandels M, Weber J (1969) The production of cellulases. Adv Chem Ser 95,391-414.

Mellor, J., Dobson, M. J., Roberts, N. A., Tuite, M. F., Emtage, J. S., White, S., Lowe, P. A., Patel, T., Kingsman, A. J. and Kingsman, S. M. (1983). Efficient synthesis of enzymatically active calf chymosin in *Saccharomyces cerevisiae*. Gene 24, 1-14.

Moes, C. J., Pretorius, I. S. and van Zyl, W. H. (1996) Cloning and expression of the clostridiumthermosulfurogenes d-xylose isomerase gene (xy1A) in *Saccharomyces cerevisiae*. Biotechnology letters 18, 269-274

Margolles-Clark E., Tenkanen, M., Nakari-Setälä, T. and Penttilä, M. (1996) Cloning of genes encoding alpha-L-arabinofuranosidase and beta-xylosidase from *Trichoderma reesei* by expression in *Saccharomyces cerevisiae*. Appl. Environ. Microbiol. 62, 3840-3846

Richard, P., Toivari, M. H. and Penttilä, M. (1999) Evidence that the gene YLR070c of *Saccharomyces cerevisiae* encodes a xylitol dehydrogenase. FEBS Letters 457, 135-138

Richard, P., Toivari, M. H. and Penttilä, M. (2000) The role of xylulokinase in *Saccharomyces cerevisiae* xylulose catabolism. FEMS Microbiol. Lett. 190, 39-43

Sarthy, A. V., McConaughy, B. L., Lobo, Z, Sundstrom, J. A., Furlong, C. E. and Hall, B. D. (1987) Expression of the *Escheria coli* xylose isomerase gene in *Saccharomyces cerevisiae*. Appl. Environ. Microbiol. 53, 1996-2000

Schründer, J., Gunge, N. and Meinhardt, M. (1996) Extranuclear expression of the bacterial xylose isomerase (xy1A) and the UDP-glucose dehydrogenase (hasB) genes in yeast with *Kluyveromyces lactis* linear killer plasmids as vectors. Current Microbiology 33, 323-330

Sedlac, M. and Ho, N. W. Y. (2001) Expression of *E. coli* araBAD operon encoding enzymes for metabolizing L-arabinose in *Saccharomyces cerevisae*. Enzyme. Microb. Technol. 28, 16-24

Shaw, D. R. D. (1956) Polyol dehydrogenases. 3. Galactitol dehydrogenase and D-iditol dehydrogenase. Biochem. J. 64, 394-405

Sherman, F., Fink, G. and Hicks, J. B. (1983) Methods in yeast genetics. A laboratory manual. Cold Spring Harbor Laboratory Press, Cold Spring Harbor, N.Y.

Shi, N. Q., Prahl, K., Hendrick, J., Cruz, J., Lu, P., Cho, J. Y., Jones, S. and Jeffries, T. (2000) Characterization and complementation of a *Pichia stipitis* mutant unable to grow on D-xylose or L-arabinose. Appl Biochem Biotechnol. 84-86:201-16

Stryer, L. (1988) Biochemistry, Freeman/ New York

Toivari, M. H., Aristidou, A., Ruohonen, L. & Penttilä, M. (2001). Conversion of xylose to ethanol by recombinant *Saccharomyces cerevisiae:* Importance of xylulo-kinase (XKS1) and oxygen availability. Metab. Eng. 3, 236-249.

Verduyn, C., van Kleef, R., Frank, J., Schreuder, J. H., van Dijken, J. P. and Scheffers, W. A. (1985) Properties of the NAD(P)H-dependent xylose reductase from the xylose-fermenting yeast *Pichia stipitis*. Biochem. J. 226, 668-677

Wang, T., Penttilä, M., Gao, P., Wang, C. and Zhong, L. (1998) Isolation and Identification of xylitol dehydrogenase gene from *Trichoderma reesei*. Chin. J. Biotechnol. 14, 179-185

Witteveen, C. F. B., Bunsink, R., van de Vondervoort, P., Dijkema, C., Swart, K. and Visser, J. (1989) L-arabinose and D-xylose catabolism in *Aspergillus niger*. J. Gen Microbiol 135, 2163-2171

Witteveen, C. F. B., Weber, F., Busink, R. and Visser, J. (1994) Isolation and characterisation of two xylitol dehydrogenases from *Aspergillus niger*. Microbiol. 140, 1679-1685

The invention claimed is:

1. A method of producing a useful product from biomass containing L-arabinose, which comprises:
   (a) providing a genetically modified fungus which is transformed with a DNA encoding an enzyme selected from the group consisting of L-arabinitol 4-dehydrogenase (LA4D) and L-xylulose reductase (LXR), each of the fungal L-arabinose pathway, wherein said fungus has an increased ability to utilize L-arabinose; and
   (b) fermenting said fungus under conditions suitable to produce said useful product,
wherein the DNA is selected from the group consisting of SEQ ID NO. 1, and SEQ ID NO. 2.

* * * * *